US008968259B2

(12) United States Patent
Veasey et al.

(10) Patent No.: US 8,968,259 B2
(45) Date of Patent: Mar. 3, 2015

(54) RESETTABLE DRIVE MECHANISM FOR A DRUG DELIVERY DEVICE

(75) Inventors: Robert Veasey, Leamington Spa (GB); George Cave, Reading (GB); Christopher Jones, Tewkesbury (GB); Garen Kouyoumjian, Leamington Spa (GB); Catherine Anne Macdonald, Ashby-de-la-Zouch (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 323 days.

(21) Appl. No.: 13/498,906

(22) PCT Filed: Sep. 29, 2010

(86) PCT No.: PCT/EP2010/064430
§ 371 (c)(1),
(2), (4) Date: Jul. 24, 2012

(87) PCT Pub. No.: WO2011/039237
PCT Pub. Date: Apr. 7, 2011

(65) Prior Publication Data
US 2012/0279329 A1      Nov. 8, 2012

(30) Foreign Application Priority Data
Sep. 30, 2009    (EP) .................................... 09171769

(51) Int. Cl.
*A61M 5/315*    (2006.01)
*F16H 19/04*    (2006.01)
*A61M 5/24*    (2006.01)

(52) U.S. Cl.
CPC .............. *A61M 5/3158* (2013.01); *A61M 5/24* (2013.01); *A61M 5/31535* (2013.01);
(Continued)

(58) Field of Classification Search
CPC .......... A61M 5/3158; A61M 5/31555; A61M 5/31535; A61M 5/31543
USPC ............................... 604/207–209, 224; 74/34
See application file for complete search history.

(56) References Cited

U.S. PATENT DOCUMENTS 1,014,706 A  *  1/1912  Houghton .......................... 74/27
3,981,204 A  *  9/1976  Starbard ............................ 74/34

(Continued)

FOREIGN PATENT DOCUMENTS

FR          2683140        5/1993
JP       2005-261685       9/2005

(Continued)

OTHER PUBLICATIONS

International Search Report for International App. No. PCT/EP2010/064430, completed Feb. 3, 2011.

(Continued)

*Primary Examiner* — Theodore Stigell
*Assistant Examiner* — Benjamin Koo
(74) *Attorney, Agent, or Firm* — McDonnell Boehnen Hulbert & Berghoff LLP

(57) ABSTRACT

The present disclosure relates to a resettable drive mechanism for use in a drug delivery device. The drug delivery device is having a distal direction and a proximal direction. The drive mechanism comprises a drive rack engaged with a drive gear, a piston rack engaged with a piston gear and coupling means for coupling the drive gear with the piston gear. In a first state of the drive mechanism, the drive gear and the piston gear are coupled and the piston rack moves in distal direction when the drive rack is moved in distal direction. In a second state of the drive mechanism, the drive gear and the piston gear are decoupled and the piston rack is moveable in proximal direction for resetting the drive mechanism.

19 Claims, 7 Drawing Sheets

(52) U.S. Cl.
CPC ...... *A61M 5/31543* (2013.01); *A61M 5/31555* (2013.01); *A61M 5/31558* (2013.01); *A61M 5/31575* (2013.01); *A61M 2005/2407* (2013.01); *A61M 2005/2488* (2013.01); *A61M 2005/3152* (2013.01)
USPC ............................................. 604/224; 74/34

(56) References Cited

U.S. PATENT DOCUMENTS

| | | | | |
|---|---|---|---|---|
| 4,465,478 | A | * | 8/1984 | Sabelman et al. ............ 604/224 |
| 2004/0210199 | A1 | | 10/2004 | Atterbury et al. |
| 2007/0093761 | A1 | | 4/2007 | Veasey et al. |
| 2009/0254060 | A1 | * | 10/2009 | Hetherington ................ 604/506 |

FOREIGN PATENT DOCUMENTS

| | | |
|---|---|---|
| WO | 98/56436 | 12/1998 |
| WO | 03/080160 | 10/2003 |
| WO | 2004/007003 | 1/2004 |

OTHER PUBLICATIONS

European Search Report for European App. No. 09171769.4, completed Mar. 30, 2010.
International Preliminary Report on Patentability for International App. No. PCT/EP2010/064430, issued Apr. 3, 2012.
Japanese Office Action for JP App. No. 2012-531400, mailed Aug. 5, 2014.

* cited by examiner

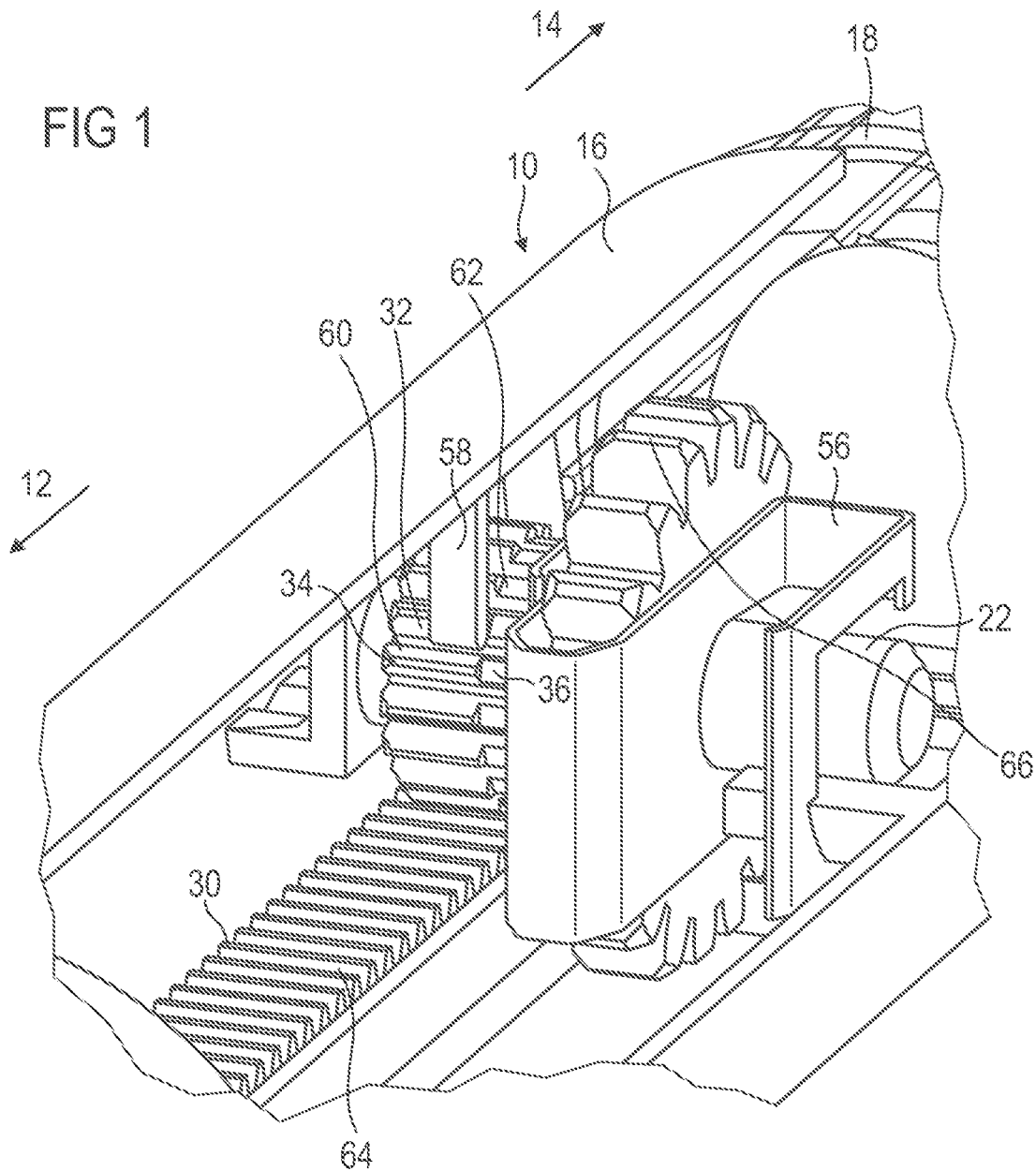

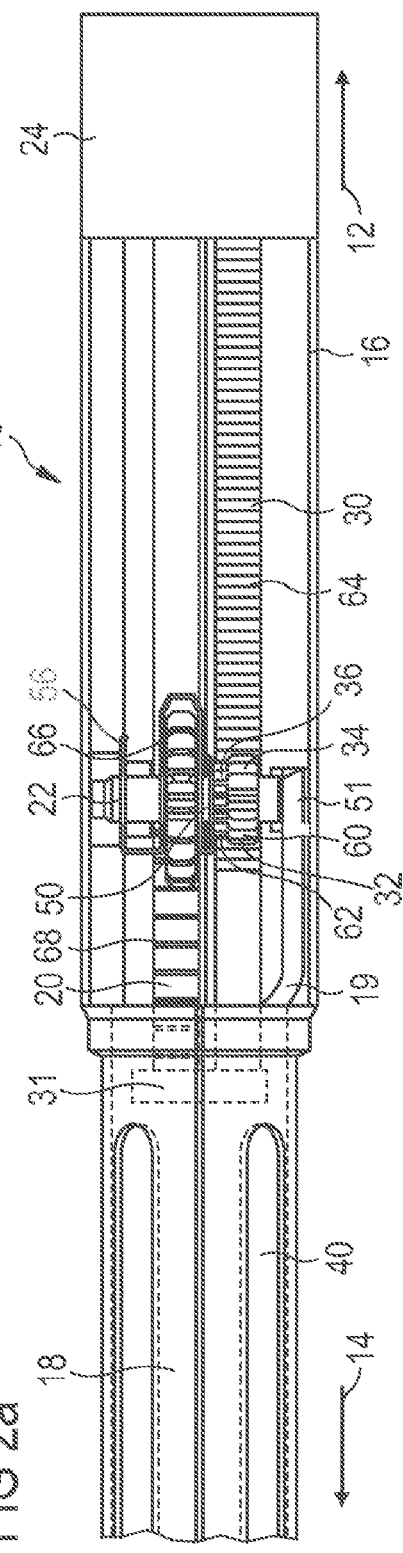

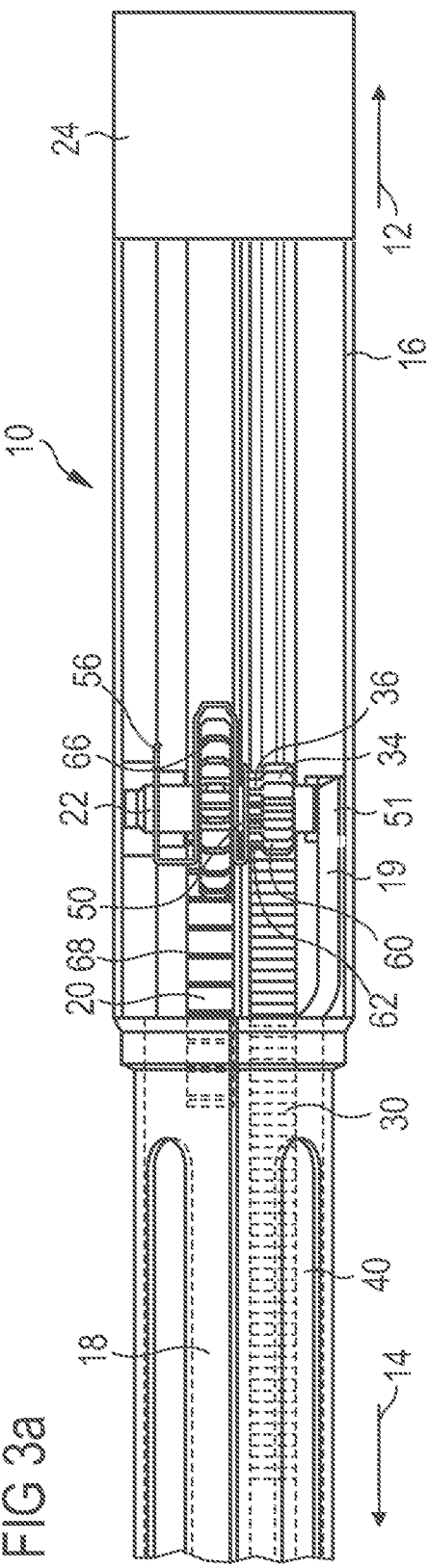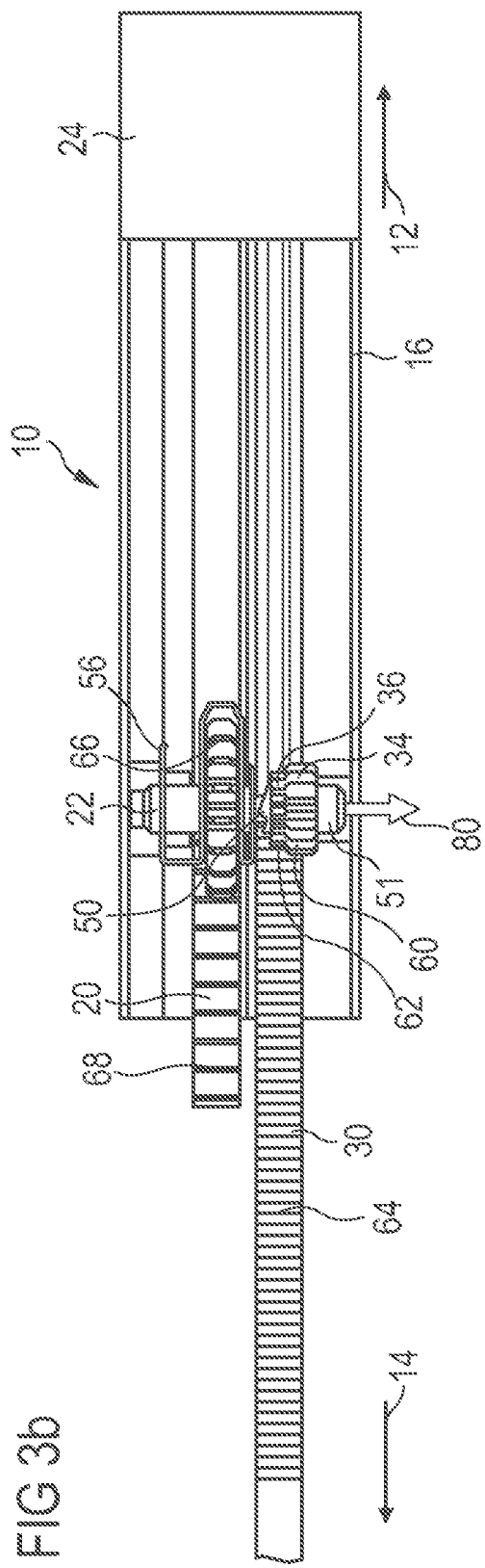

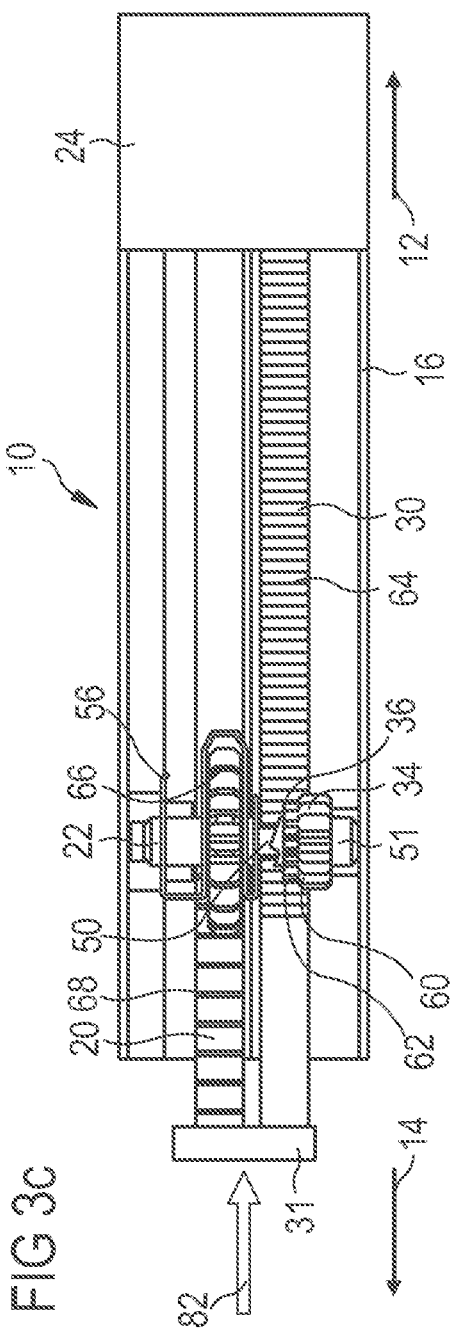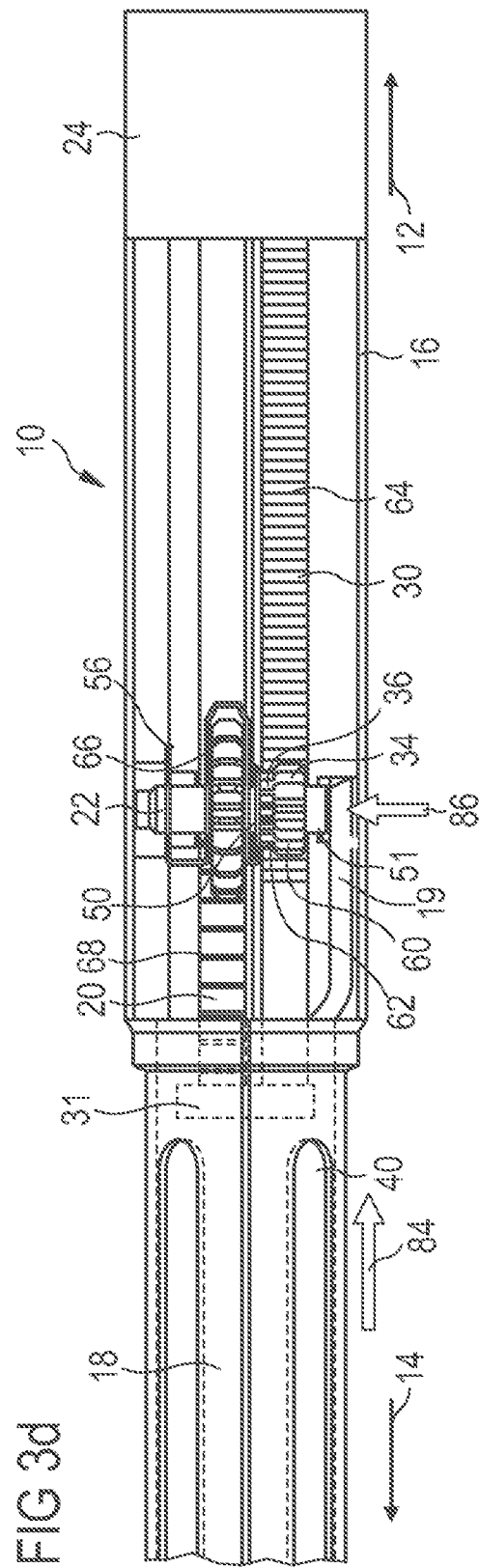

RESETTABLE DRIVE MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2010/064430 filed Sep. 29, 2010, which claims priority to European Patent Application No. 09171769.4 filed on Sep. 30, 2009. The entire disclosure contents of these applications are herewith incorporated by reference into the present application.

FIELD OF INVENTION

The present invention relates to a resettable drive mechanism for use in a drug delivery device, a method for resetting a drive mechanism and the use of a gear.

BACKGROUND

Drug delivery devices are generally known for the administration of a medicinal product, for example insulin or heparin, but also for other medicinal products for self-administration by a patient.

SUMMARY

It is an object of the present disclosure to provide a drug delivery device, which helps to improve usability.

According to a first aspect of the present disclosure, a resettable drive mechanism for use in a drug delivery device is provided. The drug delivery device has a distal direction and a proximal direction. The drive mechanism comprises a drive rack engaged with a drive gear, a piston rack engaged with a piston gear and coupling means for coupling the drive gear with the piston gear. In a first state of the drive mechanism, the drive gear and the piston gear are coupled and the piston rack moves in distal direction when the drive rack is moved in distal direction. In a second state of the drive mechanism, the drive gear and the piston gear are decoupled and the piston rack is moveable in proximal direction for resetting the drive mechanism.

The drug delivery device comprises a distal end, where a medicinal product may be dispensed out of an assembled medicament cartridge. The proximal end indicates the opposite end to the distal end.

In a first state of the assembly, the drive gear and the piston gear are coupled such that when the drive rack is moved in distal direction, the drive gear and the piston gear rotate. The rotation of the drive gear together with the piston gear causes a distal movement of the piston rack. By means of the movement of the piston rack, a bung may be driven forward in an assembled medicament cartridge, thereby dispensing a fluid medicinal product.

In the second state of the assembly, the drive gear and the piston gear are decoupled. Due to the decoupled drive gear and piston gear, the piston rack is moveable in proximal direction. By moving the piston rack in proximal direction, the drug delivery device can be reset.

In a preferred embodiment, a dose of a fluid medicinal product can be set by moving the drive rack in proximal direction, whereby the drive gear rotates with respect to the piston gear.

The drive rack may be located along the longitudinal axis of the drug delivery device coplanar with the piston rack. The drive rack may be supported such that it is only permitted to move linearly parallel to the axis of the drug delivery device.

The drive gear may be arranged such that its axis of rotation is perpendicular to the main axis of the drug delivery device. The drive gear features teeth arranged around its circumference that may be permanently engaged with teeth located at the drive rack. The engagement may be such that axial movement of the drive rack will result in rotation of the drive gear about its axle of rotation and vice versa.

An axle is arranged at a first side of the drive gear. The axle protrudes from the center of the drive gear. The drive gear may be located inside a body of the drug delivery device such that the rotational motion of the drive gear relative to the body is permitted but axial motion is not. A second side of the drive gear may comprise an aperture for the insertion of a piston gear axle. Coupling means for coupling the drive gear and the piston gear may be provided. The coupling means may be ratchet teeth.

For setting a dose of a fluid medicinal product, a button member, which may be assembled to the drive rack or part of the drive rack itself, is pulled in proximal direction with respect to the body. This causes the drive gear to rotate about its axle due to the meshed engagement between teeth located at the drive rack and the drive gear teeth.

As the drive gear rotates, the coupling means, which may include ratchet teeth that may be arranged between the drive gear and the piston gear, slip over one another. The ratchet teeth may slip over one another because the piston gear can not rotate due to a non-return member which prevents rotational movement of the piston gear in one direction. Therefore, the piston gear remains stationary while the drive gear rotates.

Furthermore, the ratchet teeth may comprise an inclination, which may be formed such that a rotational movement in one direction may overcome the ratchet teeth. In the opposite direction, the inclination of the ratchet teeth may prevent relative rotation.

The drive gear is able to move along its axis of rotation against the action of an engagement means so that the ratchet teeth can be overcome in a direction along the axis of a rotation of the gears.

In addition, the engagement between the non-return member, which is located at the body of the drug delivery device and the piston gear, ensures that the piston gear can not rotate in the same direction as the drive gear. Any torque transmitted to the piston gear by the drive gear can not result in rotation of the piston gear.

Once the drive rack is fully moved in proximal direction, the ratchet teeth between the drive gear and the piston gear may drop into an engagement position, providing the user with feedback that the dose of the fluid medicinal product has been fully set.

In another preferred embodiment, in the first state moving the drive rack in distal direction causes a movement of the piston rack in distal direction whereby a fluid medicinal product is dispensed from the medicament cartridge.

The piston gear features an axle that passes into the drive gear aperture on one side such that its axis of rotation lies along that of the drive gear. Around its circumference, the piston gear may feature a plurality of teeth. A first set of teeth may be engagable with a non-return member mounted on the body. A second set of teeth features a shorter tooth height than the first set of teeth. This ensures that the second set of teeth may not engage with the non-return member. Both sets of teeth may be in permanent engagement with the piston rack wherein the first set of teeth of the piston gear has a larger teeth length than the second set of teeth.

The piston gear can be engaged and disengaged from the non-return member by an axial motion of the piston gear. This axial motion may take place without losing engagement with the piston rack.

Once a dose of a fluid medicinal product is set the user pushes axially on the button member in a distal direction in order to dispense the fluid medicinal product out of an assembled medicament cartridge. This causes a rotation of the drive gear in the opposite direction as for setting a dose. Thereby, the drive rack moves in the distal direction.

As the drive gear rotates due to the movement of the drive rack, the coupling means between the drive gear and the piston gear interlock and cause the piston gear to rotate with the drive gear, effectively creating a compound gear.

The non return-feature allows rotation of the piston gear in the same direction as the drive gear rotates while the button member is moved in distal direction. The ratcheting of this feature over the piston gear may produce several clicks, providing feedback to the user that the fluid medicinal product is dispensed.

The rotation of the piston gear and its engagement with the teeth on the piston rack may cause the piston rack to travel in the distal direction along the axis of the drug delivery device. The movement of the piston rack may force the bung within an assembled medicament cartridge to move in distal direction and may expel a dose of a fluid medicinal product out of the medicament cartridge.

The difference in diameter of the drive gear and the piston gear acting as a compound gear produces a mechanical advantage in the system between the force input by the user on the button member and the subsequent force exerted on the cartridge bung by the distal part of the piston rack.

In a preferred embodiment, the coupling means comprise a unidirectional coupling.

The coupling means may comprise a first coupling member and a second coupling member. When a first coupling member which is located at the piston gear is engaged with a second coupling member, the first and the second coupling member ensure that rotation of the drive gear in one direction is transmitted to the piston gear.

The coupling means may comprise ratchet teeth, which allow relative rotation only in one direction. The term "unidirectional" may imply a coupling, which allows relative rotation between two components in one direction and prevents rotation relative to each other in the opposite direction. Alternatively, it may imply that a relative movement, which has not to be a rotational movement, is only possible in one direction and not in another. The non-return member and the movement of the gear also contribute to the unidirectional coupling.

In another preferred embodiment, the coupling means comprise a first coupling means located at the drive gear and a second coupling means located at the piston gear.

The coupling means can comprise a first coupling member which can be located on the drive gear and a corresponding second coupling member which can be located at the piston gear.

In a preferred embodiment the coupling means allow rotational movement relative to each other in one direction while a dose of a fluid medicinal product is set and wherein the coupling means prevent rotational movement relative to each other while a dose of a fluid medicinal product is dispensed.

For dose setting, the coupling means, which may be ratchet teeth located between the drive gear and the piston gear, slip over one another. The piston gear remains stationary because of a non-return member, which prevents rotation in one direction and which is in engagement with the piston gear. The drive gear may rotate and is able to move axially along its axis of rotation against the action of for example a gear spring so that the ratchet teeth can be overcome.

For dose dispensing, the drive gear rotates due to the movement of the drive rack. The coupling means between the drive gear and the piston gear are interlocked and may cause the piston gear to rotate with the drive gear, effectively creating a compound gear.

In another preferred embodiment, the drive mechanism comprises a non-return member to prevent rotation of a piston gear in one direction while the drive gear and the piston gear are coupled.

The non-return member may be integrally formed with the body of the drug delivery device. The non-return member can be part of the body of the drug delivery device or can be rigidly connected to the body. The non-return member should prevent a rotational movement of the piston gear in one direction, while a dose of a fluid medicinal product is being set and should enable the piston gear to be rotatable in both directions while a medicament cartridge is being replaced.

The non-return member may comprise an elastic material, which can be overcome only in one direction.

According to another preferred embodiment, the piston gear comprises a first part and a second part configured such that in the first state the non-return member is located at the first part of the piston gear and in the second state the non-return member is located at the second part of the piston gear.

A first part of the piston gear may comprise a first diameter and a first set of teeth. A second part of the piston gear may comprise a second diameter and a second set of teeth.

Due to the special shape of the piston gear, it may be possible to shift the piston gear relative to an assembled non-return member in such a way, that the non-return member is no longer engaged with the first part of the piston gear. Thereby, the piston rack may be pushed back in proximal direction.

In another preferred embodiment in the first state of the drive mechanism, the non-return member is engaged with the first part of the piston gear.

The first part comprises a set of teeth with a larger diameter than a second set of teeth located at the second part of the piston gear. The engagement with the non-return member prevents rotational movement of the piston gear in one direction and allows rotational movement of the piston gear in the other direction.

According to another preferred embodiment in the second state of the drive mechanism, the non-return member is disengaged from the first part of the piston gear.

By disengaging the non-return member from the first part of the piston gear, it is possible to rotate the piston gear in both directions.

In another preferred embodiment both the first and the second part of the piston gear comprise teeth configured to be engaged with the piston rack, which comprises teeth.

The permanent engagement between the teeth of the piston rack with both sets of teeth located at the piston gear allows that the relative position between the drive gear and the piston gear is the same while resetting the piston rack. The non-return member is disengaged from the first part of the piston gear by the displacement along the axis of rotational movement of the piston gear.

In another preferred embodiment, the drive rack is moveable in distal direction and in proximal direction.

The drive rack can be moved in one direction for setting a dose of a fluid medicinal product. For dispensing a dose of a fluid medicinal product, the drive rack may be moved in the opposite direction.

According to another preferred embodiment, the drive rack and the drive gear comprise teeth to engage with each other.

Preferably, the drive rack features a set of teeth at the distal end of the drive rack. The set of teeth extends some distance along the length of the drive rack. These teeth are designed to engage mating teeth on the drive gear.

According to another preferred embodiment for resetting the drive mechanism, an engagement means is configured to enable the piston gear to be disengaged from the drive gear and to be free to rotate relative to the drive gear and the non-return member and wherein the free rotation of the piston gear enables the piston rack to be moved in proximal direction.

There may be one or more engagement means provided. A first engagement means acts to engage the drive gear and the piston gear and a second engagement means acts to disengage the drive gear and the piston gear.

The first engagement means can be for example an elongated part of the cartridge holder which acts upon a part of the piston gear to push the piston gear towards the drive gear.

The second engagement means may be for example a spring, which can be located inside the piston gear axle and applies a separating force to the piston gear and to the drive gear by pushing the piston gear away from the drive gear. Another possible second engagement means may be a gear spring which is arranged around the drive gear and acts to separate the drive gear and the piston gear.

According to another preferred embodiment, the engagement means are configured to couple and decouple the coupling means between the drive gear and the piston gear.

Due to the engagement means, a first coupling member located on the drive gear and a second coupling member located at the piston gear may be coupled and decoupled. By means of the engagement means, the piston gear is moved towards the drive gear. Thereby, the coupling members, which may comprise ratchet teeth, couple.

In another embodiment, the engagement means are configured to decouple the drive gear and the piston gear during removal of a medicament cartridge and couple the drive gear and the piston gear during replacement of the cartridge.

After the medicament cartridge has been removed from the drug delivery device, the drive gear and the piston gear can decouple to enable the piston rack to be pushed back in proximal direction without driving the drive gear and the drive rack. The engagement means may be assembled between the drive gear and the piston gear such that a force may be applied to the piston gear, which pushes the piston gear away from the drive gear.

On the other hand, the engagement means should couple the drive gear with the piston gear to enable the drug delivery device to set and dispense a dose of a fluid medicinal product out of an assembled medicament cartridge when a medicament cartridge is present.

According to another preferred embodiment, the disengagement between the drive gear and the piston gear is achieved by the relative movement of the drive gear and the piston gear perpendicular to the proximal direction.

By applying a force, like for example by means of a spring, the piston gear may be moved relative to the drive gear and relative to the non-return member. The force displaces the piston gear along its axis of rotation such that the piston gear is disengaged from the non-return-feature. This disengagement allows a free rotation of the piston gear and enables initiating the reset of the device.

According to a second aspect of the present disclosure, a drug delivery device is provided which comprises the described resettable drive mechanism.

A drug delivery device, which comprises a resettable drive mechanism according to the present disclosure, may have many advantages for the user of such a drug delivery device.

Inter alia, the medicament cartridge is replaceable and the user may change the medicament cartridge quickly and on his own. Therefore, the drug delivery device is reusable and cost-effective for the user of the drug delivery device.

According to a third aspect of the present disclosure, a method for resetting a drive mechanism is provided. The drive mechanism comprises engagement means, a drive gear, a piston gear engaging with the drive gear and a piston rack engaging with the piston gear. The method for resetting the drive mechanism comprises the steps of disengaging the piston gear from the drive gear by the engagement means thus enabling the piston gear to rotate freely, and moving the piston rack in a proximal direction.

Preferably, once the medicament cartridge is empty, it can be replaced and the drive mechanism can be reset by axially disconnecting the cartridge holder from the body of the drug delivery device. The elongated portion of the cartridge holder counteracts to the separating force exerted by the gear spring, which is located between the drive gear and the piston gear. Thus, as the cartridge holder is removed, the piston gear moves axially, along its rotational axis, away from the drive gear under the action of the gear spring.

The axial motion of the piston gear brings the first part of the piston gear out of engagement with the non-return member, which is located at the body. Additionally, the axial motion of the piston gear may decouple the ratchet teeth between the drive gear and at the piston gear. However, the piston gear maintains the toothed engagement with the piston rack.

Once the cartridge holder is fully removed, the piston rack can be returned to the starting position by the user applying an axial force in the proximal direction to the distal end of the piston rack. As the piston rack moves axially, the piston gear is free to rotate under the toothed engagement with the piston rack.

Once the piston rack is returned to its starting position, the cartridge holder with a new cartridge is refitted axially into the device. The elongation on the cartridge holder interferes with the axle of the piston gear and forces it axially towards the drive gear against the force of the gear spring.

According to a fourth aspect of the present disclosure, the use of a gear is provided. The gear comprises a first part and a second part and is used as a dispense gear and as a reset gear. The first part of the gear comprises a first diameter and a first toothing. The second part of the gear comprises a second diameter and a second toothing. The first diameter is greater than the second diameter. When used in a first step as a dispense gear, the first toothing of the gear is engaged with a non-return member which prevents rotation of the gear relative to the non-return member in one direction and allows for rotation in the opposite direction. When used in a second step as a reset gear the first toothing of the gear is disengaged from the non-return member allowing for rotation in the one direction.

Due to the shape of the gear, the resetting of a piston rack is very easy. Such a drug delivery device is cost-effective because no additional component may be needed for having a separate reset-mechanism. The gear can be used as a drive gear and as a reset gear.

According to another preferred embodiment, the gear, when used as a reset gear, is rotatable in both directions relative to the non-return member. The first and the second toothing of the two parts of the gear are configured to engage with a rack.

The set of teeth, which may be circumferentially arranged at the second part of the piston gear, could be formed such that the non-return member can not engage with the teeth and thereby block the rotation of the piston gear when used as a reset gear. Both parts of the piston gear should be able to engage with the piston rack.

The terms "medicinal product", "drug" and "fluid medicinal product", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
   H-(Lys)4-des Pro36, des Pro37 Exendin-4(1-39)-NH2,
   H-(Lys)5-des Pro36, des Pro37 Exendin-4(1-39)-NH2,
   des Pro36 [Asp28] Exendin-4(1-39),
   des Pro36 [IsoAsp28] Exendin-4(1-39),
   des Pro36 [Met(O)14, Asp28] Exendin-4(1-39),
   des Pro36 [Met(O)14, IsoAsp28] Exendin-4(1-39),
   des Pro36 [Trp(O2)25, Asp28] Exendin-4(1-39),
   des Pro36 [Trp(O2)25, IsoAsp28] Exendin-4(1-39),
   des Pro36 [Met(O)14 Trp(O2)25, Asp28] Exendin-4(1-39),
   des Pro36 [Met(O)14 Trp(O2)25, IsoAsp28] Exendin-4(1-39); or
   des Pro36 [Asp28] Exendin-4(1-39),
   des Pro36 [IsoAsp28] Exendin-4(1-39),
   des Pro36 [Met(O)14, Asp28] Exendin-4(1-39),
   des Pro36 [Met(O)14, IsoAsp28] Exendin-4(1-39),
   des Pro36 [Trp(O2)25, Asp28] Exendin-4(1-39),
   des Pro36 [Trp(O2)25, IsoAsp28] Exendin-4(1-39),
   des Pro36 [Met(O)14 Trp(O2)25, Asp28] Exendin-4(1-39),
   des Pro36 [Met(O)14 Trp(O2)25, IsoAsp28] Exendin-4(1-39), wherein the group -Lys6-NH2 may be bound to the C-terminus of the Exendin-4derivative;

or an Exendin-4derivative of the sequence
   H-(Lys)6-des Pro36 [Asp28] Exendin-4(1-39)-Lys6-NH2,
   des Asp28 Pro36, Pro37, Pro38Exendin-4(1-39)-NH2,
   H-(Lys)6-des Pro36, Pro38 [Asp28] Exendin-4(1-39)-NH2,
   H-Asn-(Glu)5des Pro36, Pro37, Pro38 [Asp28] Exendin-4(1-39)-NH2,
   des Pro36, Pro37, Pro38 [Asp28] Exendin-4(1-39)-(Lys)6-NH2,
   H-(Lys)6-des Pro36, Pro37, Pro38 [Asp28] Exendin-4(1-39)-(Lys)6-NH2,
   H-Asn-(Glu)5-des Pro36, Pro37, Pro38 [Asp28] Exendin-4(1-39)-(Lys)6-NH2,
   H-(Lys)6-des Pro36 [Trp(O2)25, Asp28] Exendin-4(1-39)-Lys6-NH2,
   H-des Asp28 Pro36, Pro37, Pro38 [Trp(O2)25] Exendin-4(1-39)-NH2,
   H-(Lys)6-des Pro36, Pro37, Pro38 [Trp(O2)25, Asp28] Exendin-4(1-39)-NH2,
   H-Asn-(Glu)5-des Pro36, Pro37, Pro38 [Trp(O2)25, Asp28] Exendin-4(1-39)-NH2,
   des Pro36, Pro37, Pro38 [Trp(O2)25, Asp28] Exendin-4(1-39)-(Lys)6-NH2,
   H-(Lys)6-des Pro36, Pro37, Pro38 [Trp(O2)25, Asp28] Exendin-4(1-39)-(Lys)6-NH2,
   H-Asn-(Glu)5-des Pro36, Pro37, Pro38 [Trp(O2)25, Asp28] Exendin-4(1-39)-(Lys)6-NH2,
   H-(Lys)6-des Pro36 [Met(O)14, Asp28] Exendin-4(1-39)-Lys6-NH2,
   des Met(O)14 Asp28 Pro36, Pro37, Pro38 Exendin-4(1-39)-NH2,
   H-(Lys)6-desPro36, Pro37, Pro38 [Met(O)14, Asp28] Exendin-4(1-39)-NH2,
   H-Asn-(Glu)5-des Pro36, Pro37, Pro38 [Met(O)14, Asp28] Exendin-4(1-39)-NH2,
   des Pro36, Pro37, Pro38 [Met(O)14, Asp28] Exendin-4(1-39)-(Lys)6-NH2,
   H-(Lys)6-des Pro36, Pro37, Pro38 [Met(O)14, Asp28] Exendin-4(1-39)-(Lys)6-NH2,
   H-Asn-(Glu)5 des Pro36, Pro37, Pro38 [Met(O)14, Asp28] Exendin-4(1-39)-(Lys)6-NH2,
   H-Lys6-des Pro36 [Met(O)14, Trp(O2)25, Asp28] Exendin-4(1-39)-Lys6-NH2,
   H-des Asp28 Pro36, Pro37, Pro38 [Met(O)14, Trp(O2)25] Exendin-4(1-39)-NH2,
   H-(Lys)6-des Pro36, Pro37, Pro38 [Met(O)14, Asp28] Exendin-4(1-39)-NH2,
   H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the invention is described in further detail with reference to the drawings, wherein FIG. 1 shows a three-dimensional cut-away view of the arrangement of the gears;

FIG. 2a shows a sectional view of a drug delivery device before setting a dose of a fluid medicinal product;

FIG. 2b shows a sectional view of the drug delivery device while setting a dose of a fluid medicinal product;

FIG. 3a shows a sectional view of a drug delivery device when the cartridge is empty;

FIG. 3b shows a sectional view of a drug delivery device after the cartridge holder is removed;

FIG. 3c shows a sectional view of a drug delivery device while the piston rack is returned;

FIG. 3d shows a sectional view of a drug delivery device while the cartridge holder is refitted;

DETAILED DESCRIPTION

Figure 2C:
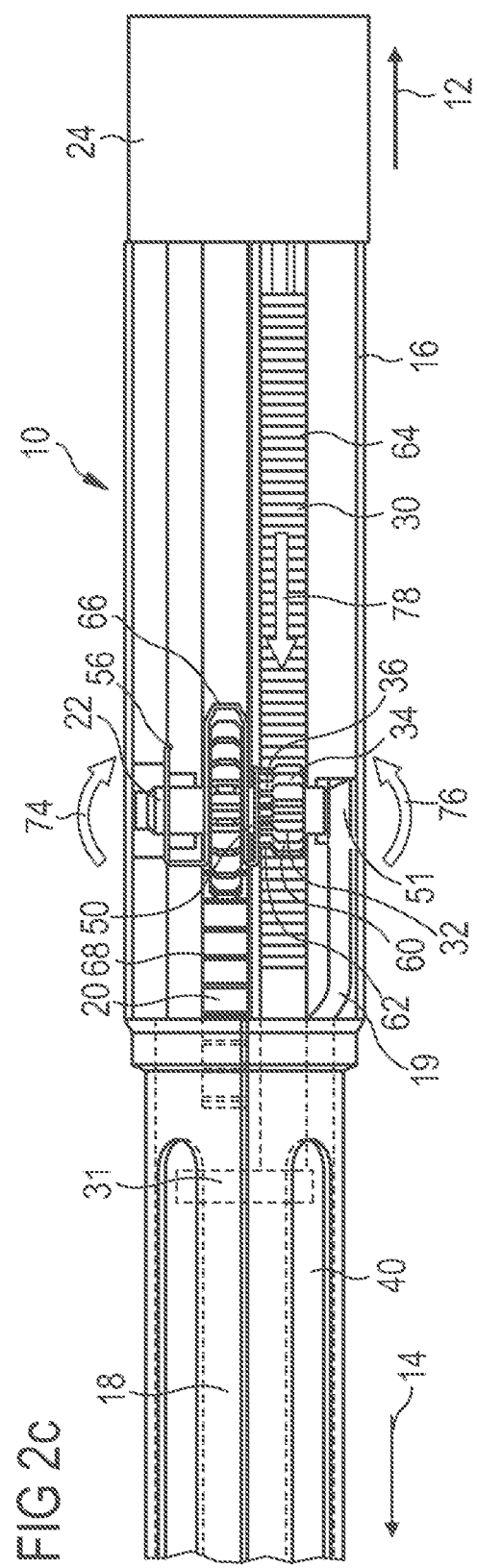
FIG. 2c shows a sectional view of a drug delivery device during dispense of a dose of a fluid medicinal product.

Some preferred embodiments of the drug delivery device according to the present disclosure will now be discussed with reference to FIG. 1, FIG. 2a, 2b, 2c, FIGS. 3a, 3b, 3c and 3d, FIGS. 4a and 4b and FIGS. 5 and 6. Identical reference numerals denote identical or comparable components.

FIG. 1 shows a three-dimensional cut-away view of the drug delivery device according to one embodiment of the present disclosure.

The drug delivery device 10 comprises a distal end 14, where the fluid medicinal product may be dispensed out of an assembled medicament cartridge, which is not explicitly shown, and a proximal end 12, which indicates the opposite end of the distal end 14.

A housing of the drug delivery device 10 comprises two parts, a body 16 and a cartridge holder 18. The cartridge holder 18 may be removed and refitted by the user. Additionally, the cartridge holder 18 is connected to the body 16 such that the connection may take the operational loads seen by the drug delivery device 10.

During use, the cartridge holder 18 is permanently attached to the body 16. Threads or a bayonet lock may connect the body 16 and the cartridge holder 18.

The body 16 comprises mounting positions for a piston gear 32, for a gear spring 56 and for a drive gear 22. The mounting positions allow rotation of both gears around their axes of rotation, axial motion of the piston gear along its axis of rotation and a fixed position of the gear spring 56. Here, the drive gear is held in position by the gear spring 56 and engagement of the axis in the body on one side and in the piston gear on the other side.

The shown drug delivery device 10 is a pen-type injector. Within the cartridge holder 18, a medicament cartridge, which is not shown, is located, which is containing a number of doses of a fluid medicinal product. The fluid medicinal product may be injected by means of a needle, which is not explicitly shown, and which may be attached to the distal end of the cartridge holder 18.

The drive mechanism comprises, inter alia, a drive gear 22 having teeth 66, a piston gear 32, a piston rack 30, a non-return member 58 and engagement means. The non-return member 58 has a fixed position relative to the body 16. The non-return member 58 can be mounted to the body 16 of the drug delivery device 10. The engagement between the body 16 and the non-return member 58 is such that the non-return member 58 can deflect along the axis of the device in one direction only, thereby disengaging from the first toothing 60 of the piston gear 32 and thus allowing the piston gear 32 to rotate. A movement in the other direction is blocked, thereby blocking rotational movement of the piston gear 32.

A button member, which is not explicitly shown, is located at the proximal end 12 of the drive rack which is also not explicitly shown. The button member enables the user to operate the drug delivery device 10.

The piston gear 32 comprises two parts, a first part 34 having a first toothing 60 and a first diameter and a second part 36 having a second toothing 62 and a second diameter.

The engagement means comprise a first and a second engagement means. The first engagement means, which is not explicitly shown, acts in a way to engage the piston gear 32 and the drive gear 22. The second engagement means acts in a way to separate the drive gear 22 and the piston gear 32 axially.

The first engagement means may be an elongation of the cartridge holder. The second engagement means, which comprises a gear spring 56, may be arranged between the drive gear 22 and the piston gear 32. The spring force is reacted by the mounting of one side of the gear spring 56 to the inside of the body 16. The piston gear 32 and the drive gear 22 can be held together against the action of the gear spring 56 by the axial interference between the piston gear 32 and an elongation 19 of the cartridge holder 18.

The piston rack 30 is located along the main axis of the drug delivery device 10. The distal end 31 of the piston rack 30 abuts the bung of an assembled medicament cartridge, wherein the bung and the medicament cartridge are not explicitly shown.

The piston rack 30 features a set of teeth 64 that extend axially along the length of the surface of the piston rack 30. The piston rack 30 is supported in the drug delivery device 10 such that it is only permitted to move linearly parallel to the longitudinal axis of the drug delivery device 10. Torque can be converted to a linear force, and vice versa, by meshing the teeth 64 of the piston rack 30 with the toothing 60, 62 of the piston gear 32.

FIG. 2a shows a sectional view of a drug delivery device before setting a dose of a fluid medicinal product.

The drug delivery device shown in FIG. 2a is substantially the same as in FIG. 1.

At the distal end of the drug delivery device 10 a button member 24 may be mounted to the distal end of the drive rack. The fluid medicinal product may be injected by means of a needle unit which is not explicitly shown, and which can be attached to the distal end 14 of the drug delivery device 10.

The engagement means comprise a first and a second engagement means. The first engagement means acts in a way to engage the piston gear 32 and the drive gear 22. The second engagement means acts in a way to disengage the drive gear 22 and the piston gear 32.

The first engagement means is an elongated part of the cartridge holder which acts upon a part 51 of the piston gear 32, thereby pushing the piston gear 32 towards the drive gear 22. The second engagement means comprises a gear spring 56 which acts to separate the drive gear 22 and the piston gear 32.

The piston gear 32 comprises two parts, a first part 34 having a first toothing 60 and a first diameter and a second part 36 having a second toothing 62 and a second diameter. Between the drive gear 22 and the piston gear 32, coupling means 50 are located, which couple the drive gear 22 and the piston gear 32. The piston rack 30 comprises a distal end 31, which abuts a bung of a medicament cartridge 40, wherein the bung is not explicitly shown.

FIG. 2b shows a sectional view of a drug delivery device while setting a dose of a fluid medicinal product.

The shown drug delivery device 10 is mainly the same as in FIG. 2a with the difference that FIG. 2b shows the drug delivery device 10 while a dose of a fluid medicinal product is set.

To set a dose of a fluid medicinal product, the user pulls the button member 24 in proximal direction 12. Due to a connection between the button member 24 and the drive rack 20, the drive rack 20 is moved in proximal direction 12.

Since the teeth 66 on the drive gear 22 and the teeth 68 on the drive rack 20 are engaged with each other, the movement of the button member 24 causes a rotation of the drive gear 22 in a direction 72.

The drive gear 22 is coupled to the piston gear 32 by means of unidirectional coupling means 50, which comprise ratchet teeth that are not explicitly shown. By rotating the drive gear 22 in the first direction of rotational movement, the ratchet teeth between the drive gear 22 and the piston gear 32 slip over one another. Due to a non-return member, which is not explicitly shown, the piston gear 32 remains stationary while the drive gear 22 rotates relative to the piston gear. The drive gear 22 is able to move axially along its axis of rotation against the action of the gear spring 56 so that the ratchet teeth of the coupling means can be overcome.

FIG. 2c shows a sectional view of a drug delivery device during dispense of a dose of a fluid medicinal product.

The shown drug delivery device 10 is mainly the same as in FIGS. 2a and 2b, with the difference that FIG. 2c shows the drug delivery device 10 while a dose of a fluid medicinal product is being dispensed.

To dispense a dose of a fluid medicinal product, the user pushes the button member 24 in distal direction 14. Due to a connection between the button member 24 and the drive rack 20, the drive rack 20 is moved in distal direction 14.

Since the teeth 66 on the drive gear 22 and the teeth 68 on the drive rack 20 are engaged with each other, the movement of the button member 24 causes a rotation of the drive gear 22 in a direction 74.

The drive gear 22 is coupled to the piston gear 32 by means of a unidirectional coupling means 50, which comprises ratchet teeth, which are not explicitly shown.

As the drive gear 22 rotates in the distal direction 14, and as the ratchet teeth between the drive gear 22 and the piston gear 32 are coupled, the piston gear 32 rotates in the direction which is allowed by the non-return member and together with the drive gear 22, effectively creating a compound gear.

Since the toothing 60, 62 on the piston gear 32 and the teeth 64 on the piston rack 30 are engaged with each other, the rotation of the piston gear 32 in the direction 76 causes a movement of the piston rack 30 in the direction 78.

Thereby, the distal end 31 of the piston rack 30 is moved in distal direction 14 and abuts a bung, which is not explicitly shown, in the assembled medicament cartridge 40. Thereby, the bung is moved in distal direction 14. Due to the distal movement of the bung, a dose of a fluid medicinal product is dispensed out of the medicament cartridge 40.

FIG. 3a shows a sectional view of a drug delivery device when the cartridge is empty.

The drug delivery device 10 shown in FIG. 3a is mainly the same as in FIG. 2c, with the difference that the medicament cartridge 40 is empty.

The drug delivery device 10 is formed such that it is possible for a user to remove the empty medicament cartridge 40 and to assemble a new medicament cartridge. The steps how to replace the medicament cartridge and to reset the drive mechanism are now described with reference to FIGS. 3b, 3c and 3d.

FIG. 3b shows a sectional view of a drug delivery device according to FIG. 3a after the cartridge holder is removed.

After the cartridge holder 18 has been removed, the drive gear 22 is disengaged from the piston gear 32. This disengagement separates the coupling means 50 and the piston gear 32 is moved in an axial direction 80 to its axis of rotation, away from the drive gear 22 under the action of the gear spring 56, which acts to disengage the drive gear 22 and the piston gear 32.

The movement of the piston gear 32 in axial direction 80 along its rotational axis brings the piston gear 32 out of engagement with the non-return member on the body 16, wherein the non-return member is not explicitly shown. The piston gear 32 maintains its toothed engagement with the piston rack 30.

FIG. 3c shows a sectional view of a drug delivery device while the piston rack is being returned.

The shown drug delivery device 10 is mainly the same as in FIG. 3b, with the difference that FIG. 3c shows the drug delivery device 10 while the piston rack 30 is moved back to its starting position, which can be seen in FIG. 2a.

The user applies an axial force in the proximal direction 12 to the distal end 31 of the piston rack 30, thereby causing a movement of the piston rack 30 in the direction 82. As the piston rack 30 moves axially, the piston gear 32 is free to rotate under the toothed engagement with the piston rack 30.

FIG. 3d shows a sectional view of a drug delivery device when the cartridge holder is refitted.

The shown drug delivery device 10 is mainly the same as in FIG. 3c, with the difference that FIG. 3c shows the drug delivery device 10 after the piston rack 30 has been moved back to its starting position and while the cartridge holder 18 is refitted.

A movement in axial direction 84 now refits the cartridge holder 18, which comprises a new medicament cartridge 40, to the drug delivery device 10. An elongation, which is not explicitly shown and which is located at the cartridge holder 18 interferes with a part 51 of the axle of the piston gear 32. Thereby, the piston gear moves in an axial direction 86 along its axis of rotational movement towards the drive gear 22 and against the force of the gear spring 56. Due to the movement of the piston gear, the drive gear 22 and the piston gear 32 are recoupled.

Figure 4A:
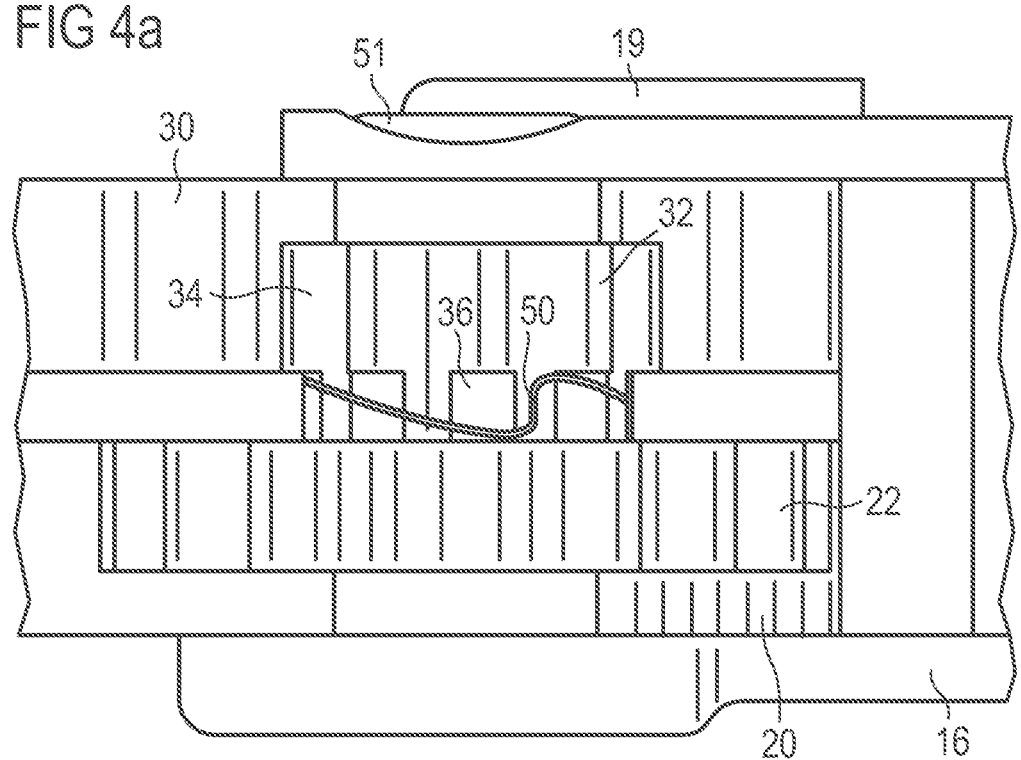
FIG. 4a shows a cross-sectional view of the drive gear and the piston gear while the coupling means are coupled.

FIG. 4a shows a sectional view of the drive gear and the piston gear while the coupling means are coupled.

The coupling means 50 comprise a first coupling member 52 and a second coupling member 54. Both coupling members 52, 54, comprise ratchet teeth.

The engagement means comprise two parts, a first part, which acts to engage the drive gear 22 and the piston gear 32 and a second part, which acts to disengage the drive gear 22 and the piston gear 32.

By means of an elongation 19 of the cartridge holder, the drive gear 22 and the piston gear 32 are engaged with each other. The drive gear 22 is able to move along its axis of rotation against the action of a part of the second part of the engagement means, which is a spring 55, so that the coupling means 50 can be overcome.

The non-return member (see FIG. 1) which is located inside the body 16 of the drug delivery device, is engaged with the first part 34 of the piston gear 32, thereby blocking rotation of piston gear 32 and blocking movement of the piston rack 30 in one direction.

Figure 4B:
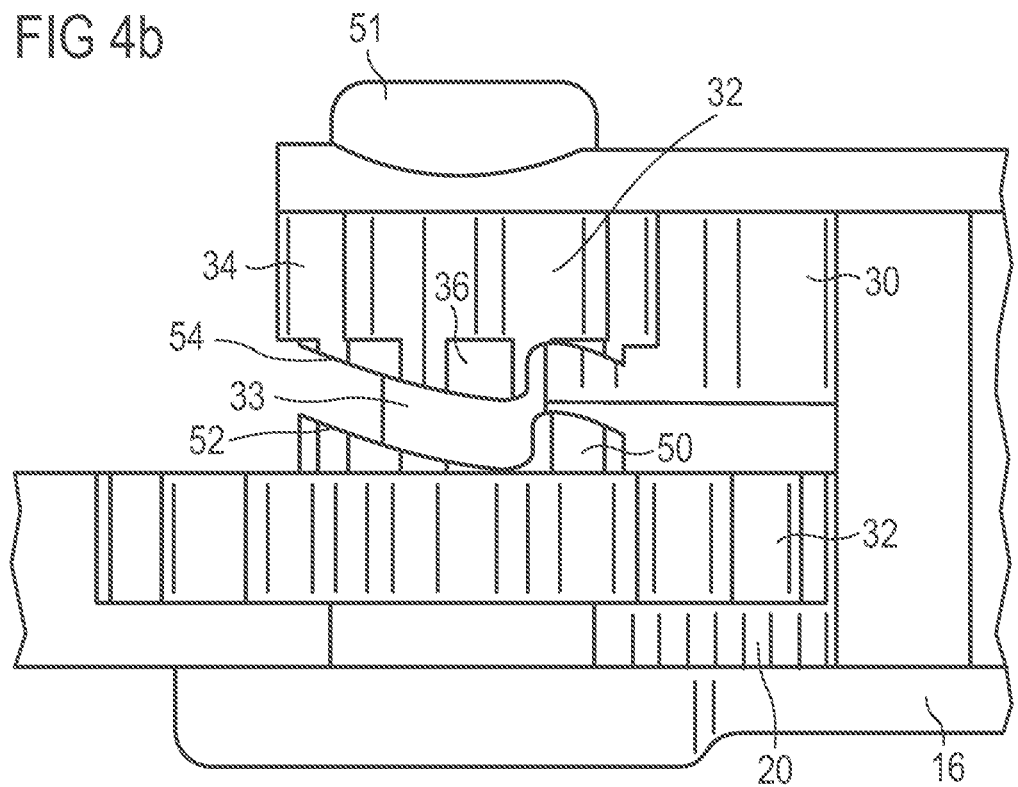
FIG. 4b shows a cross-sectional view of the drive gear and the piston gear while the coupling means are decoupled.

FIG. 4b shows a sectional view of the drive gear 22 and the piston gear 32 while the coupling means 50 are decoupled.

The shown drive gear and piston gear are substantially the same as shown in FIG. 4a with the difference that the elongated part 19 of the cartridge holder has been removed.

In a first direction of rotational movement, the ratchet teeth are inclined such that they can be overcome and enable the gears 22, 32 to rotate relative to each other. In the other direction, the inclination of the ratchet teeth is such that they can not be overcome, thereby blocking relative rotation of the gears 22, 32.

As can be seen in combination with FIG. 1, the first part 34 of the piston gear 32, which is located inside the body 16 of the drug delivery device, is disengaged from the non-return member 58, thereby allowing the piston gear 32 to be free to rotate in both directions. While the piston gear is held in this position relative to the non-return member 58 by the action of the gear spring 56, the user is able to push the piston rack 30 back into a starting position. Alternative embodiments could have the non-return member 58 as the moving component while the piston gear 32 does not move axially for disengagement with the non-return member 58.

Figure 5:
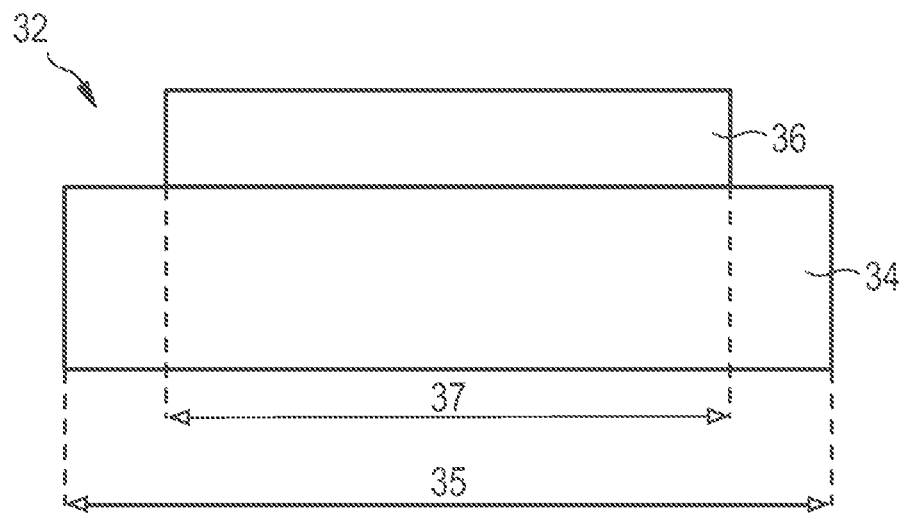
FIG. 5 shows a cross-sectional view of the piston gear.

FIG. 5 shows a cross-sectional view of the piston gear 32.

The piston gear 32 comprises two parts. A first part 34 of the piston gear 32 has a first diameter 35 and the second part 36 of the piston gear 32 has a second diameter 37. The first diameter 35 is larger than the second diameter 37.

Figure 6:
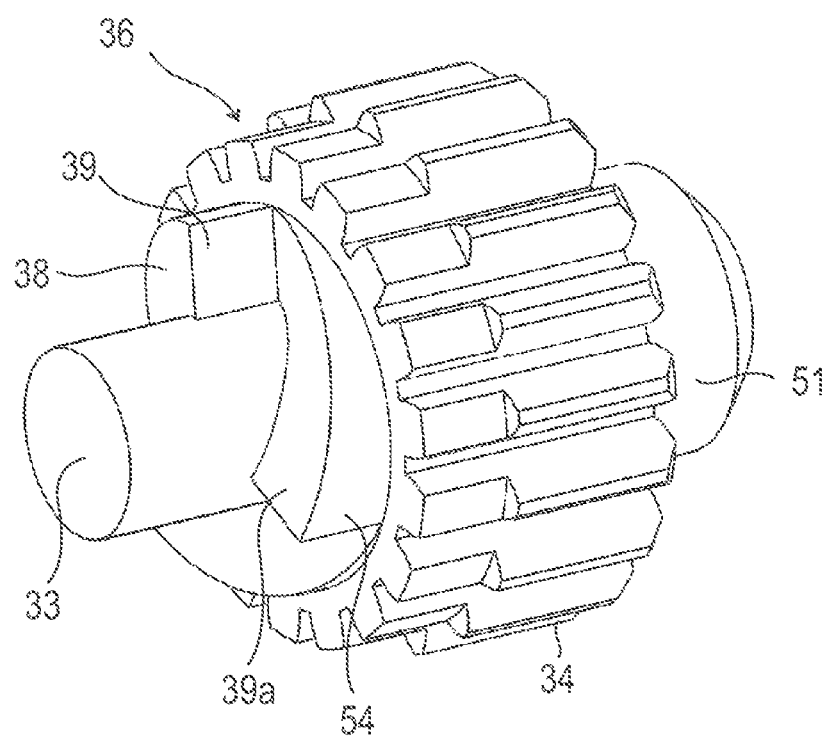
FIG. 6 shows a three-dimensional view of the piston gear.

FIG. 6 shows the piston gear having a first part 34 and a second part 36, both parts featuring teeth. The teeth of the first part are larger than the teeth of the second part. Both the teeth of the first as well of the second part are suited to engage with the piston rack. The difference in size of the teeth is chosen such that the teeth of the first part engage with the non-return member when being aligned with it while the teeth of the second part do not engage with the non-return member, irrespective whether aligned or not. Second coupling members 54 are provided on one side of the gear, the second coupling members being formed for engagement with according first coupling members of the drive gear. The second coupling members 54 comprise coupling ratchet teeth 38, each of the teeth 38 featuring a front face 39 arranged for abutment with an according counterpart of the first coupling members of the drive gear when rotated in one direction. The second coupling members also comprise an inclined surface 39a allowing a sliding movement of the first coupling members relative to the second coupling members when rotated in the opposite direction. The inclined surface 39a is inclined with respect to the axle 33 of the piston gear.

In an embodiment, the first coupling members of the drive gear may have substantially the same shape as shown in FIG. 6 i.e. the form of ratchet teeth, however being mirrored with respect to a plane perpendicular to the axle 33 in order to allow form fitting engagement of the coupling members when rotated in one direction.

The present examples are to be considered illustrative and not restrictive and the invention is not to be limited to the details given herein, but may be modified within the scope and equivalence of the appended claims.

The invention claimed is:

1. A resettable drive mechanism for use in a drug delivery device having a distal end and a proximal end, wherein the drive mechanism comprises
   a drive rack engaged with a drive gear:
   a piston rack engaged with a piston gear and having a first part and a second part;
   a coupling coupling the drive gear with the piston gear; and
   a non-return member operably engaged with the piston gear to prevent rotation of the piston gear in one direction while the drive gear and the piston gear are coupled;
   wherein in a first state of the drive mechanism,
      i) the drive gear and the piston gear are coupled and the piston rack moves in distal direction when the drive rack is moved in distal direction; and
      ii) the non-return member is located at the first part of the piston gear, and
   wherein in a second state of the drive mechanism,
      i) the drive gear and the piston gear are decoupled and the piston rack is moveable in proximal direction for resetting the drive mechanism; and
      ii) the non-return member is located at the second part of the piston gear.

2. A resettable drive mechanism according to claim 1, wherein a dose of a fluid medicinal product can be set by moving the drive rack in a proximal direction whereby the drive gear rotates with respect to the piston gear.

3. A resettable drive mechanism according to claim 1, wherein in the first state moving the drive rack in a distal direction causes a movement of the piston rack in distal direction whereby a fluid medicinal product is dispensed from an assembled medicament cartridge.

4. A resettable drive mechanism according to claim 1, wherein the coupling comprise a unidirectional coupling.

5. A resettable drive mechanism according to claim 1, wherein the coupling comprise a first coupling member located at the drive gear and a second coupling member located at the piston gear.

6. A resettable drive mechanism according to claim 5, wherein the coupling allows rotational movement of the first coupling member relative to the second coupling in one direction while a dose of a fluid medicinal product is set and wherein the coupling prevents rotational movement of the first coupling member relative to the second coupling while a dose of a fluid medicinal product is dispensed.

7. A resettable drive mechanism according to claim 1, wherein in the first state of the drive mechanism, the non-return member is engaged with the first part of the piston gear.

8. A resettable drive mechanism according to claim 7, wherein in the second state of the drive mechanism the non-return member is disengaged from the first part of the piston gear.

9. A resettable drive mechanism according to claim 1, wherein both the first and the second parts of the piston gear comprise a toothing configured to be engaged with the piston rack which comprises teeth.

10. A resettable drive mechanism according to claim 1, wherein the drive rack is moveable in a distal direction and in a proximal direction.

11. A resettable drive mechanism according to claim 1, wherein the drive rack and the drive gear comprise teeth to engage with each other.

12. A resettable drive mechanism according to claim 1, comprising an engagement mechanism configured to enable the piston gear to be disengaged from the drive gear and to be free to rotate relative to the drive gear and the non-return member and wherein the free rotation of the piston gear enables the piston rack to be moved in proximal direction.

13. A resettable drive mechanism according to claim 12, wherein the engagement mechanism is further configured to couple and decouple the coupling between the drive gear and the piston gear.

14. A resettable drive mechanism according to claim 13, wherein the engagement mechanism is further configured to decouple the drive gear and the piston gear during removal of a medicament cartridge and couple the drive gear and piston gear during replacement of the medicament cartridge.

15. A resettable drive mechanism according to claim 13, wherein the disengagement between the drive gear and the piston gear is achieved by the relative movement of the drive gear and the piston gear perpendicular to the proximal direction.

16. A drug delivery device comprising the resettable drive mechanism according to claim 1.

17. A method for resetting the resettable drive mechanism of claim 1, the method comprising an engagement mechanism, a drive gear, a piston gear engaging with the drive gear and a piston rack engaging with the piston gear, the method comprising the steps of: disengaging the piston gear from the drive gear by the engagement mechanism, thus enabling the piston gear to rotate freely and moving the piston rack in a proximal direction, the movement being enabled by the decoupling of the piston gear and the drive gear.

18. A method of using the piston gear of the resettable drive mechanism according to claim 1 as both a dispense gear and as a reset gear, the piston gear comprising a first part and a second part, the first part comprising a first diameter and a first toothing, the second part comprising a second diameter and a second toothing, wherein the first diameter is greater than the second diameter, the method comprising using herein the gear in a first dispensing step, wherein the first toothing of the gear is engaging a non-return member preventing rotation of the gear relative to the non-return member in one direction and rotating the gear in the opposite direction, and using the gear in a second step as a reset gear, wherein the first toothing of the gear is disengaged from the non-return member allowing rotation of the gear in the one direction.

19. The method of claim 18, wherein using the piston gear as a reset gear, rotating the piston gear in both directions relative to the non-return member, wherein the first and the second toothing of the two parts of the piston gear are engaging a rack.

* * * * *